(12) United States Patent
Olivares

(10) Patent No.: US 6,564,800 B1
(45) Date of Patent: May 20, 2003

(54) NASAL AIR PASSAGE DEVICE

(76) Inventor: Juan Rodriguez Olivares, P.O. Box 3893, Corpus Christi, TX (US) 78463

( * ) Notice: Subject to any disclaimer, the term of this patent is extended or adjusted under 35 U.S.C. 154(b) by 0 days.

(21) Appl. No.: 09/665,977

(22) Filed: Sep. 20, 2000

(51) Int. Cl.[7] .................. A61G 10/00; A61M 16/00; A62B 7/10; A62B 23/02
(52) U.S. Cl. ................... 128/206.11; 128/200.24; 128/200.26; 128/201.18; 128/206.18; 128/207.18; 606/199; 606/204.95; 604/94.01
(58) Field of Search .............. 128/200.26, 201.18, 128/206.11, 206.18, 207.18, 200.24; 606/199, 204.45; 604/94.01

(56) References Cited

U.S. PATENT DOCUMENTS

| 1,256,188 | A | | 2/1918 | Wilson | |
|---|---|---|---|---|---|
| 2,010,485 | A | * | 8/1935 | Heath | 606/199 |
| 2,569,743 | A | | 10/1951 | Carlock | |
| 2,672,138 | A | | 3/1954 | Carlock | |
| 2,751,906 | A | * | 6/1956 | Irvine | 128/206.11 |
| 3,424,152 | A | | 1/1969 | Kuhlman | |
| 3,935,859 | A | | 2/1976 | Doyle | |
| 4,221,217 | A | | 9/1980 | Amezcua | |
| 4,887,597 | A | * | 12/1989 | Holland | 128/206.11 |
| 5,665,104 | A | * | 9/1997 | Lee | 128/200.24 |
| 5,775,335 | A | * | 7/1998 | Seal | 128/204.12 |
| 6,004,342 | A | * | 12/1999 | Filis | 606/199 |
| 6,216,694 | B1 | * | 4/2001 | Chen | 128/205.27 |
| 6,270,512 | B1 | * | 8/2001 | Rittmann | 128/207.18 |
| 6,386,197 | B1 | * | 5/2002 | Miller | 128/200.24 |

* cited by examiner

Primary Examiner—Weilun Lo
Assistant Examiner—Michael Mendoza
(74) Attorney, Agent, or Firm—George S. Gray

(57) ABSTRACT

A nasal air passage device is provided that includes connected tubes for insertion into the nostrils. The tubes support the nostrils' interior walls, allowing an increased amount of air to pass through the nostrils, particularly during sleep. Each tube has an exterior surface that has nonconformities, such as mound-shaped, including bubble-shaped, and ridge-shaped protrusions, and the like, that are distributed in a substantially uniform manner across the exterior surface. The nonconformities cause discontinuities between the exterior surface area and the nostril interior wall tissue, thus reducing the tendency to dry and stick. The nonconformities can be arranged in substantial alignment or randomly, can be uniform or varied in size, and can be resilient or inelastic. Each tube has a forward and rearward end that is inwardly tapered, thus eliminating the presentation of a right-angled forward or rearward end to the nostril interior wall tissues. This reduces the disruption and dislocation of such tissues. The tapers can be flat, arcuate, or arcuate and extending such that a semicircular cross-sectional profile is presented at the tube forward end. The tubes and nonconformities can be resilient or inelastic. The tubes are connected in the preferred embodiment, although each tube can be independently utilized, in other embodiments. The connecting member is sized to allow the tubes to be completely insertable into the nostrils, and can be flexible or stiff. In another embodiment only one tube is provided, which includes a retrieval member. A smooth surface is used in another embodiment.

24 Claims, 14 Drawing Sheets

NASAL AIR PASSAGE DEVICE

BACKGROUND OF THE INVENTION

1. Field of the Invention

The present invention relates generally to nasal devices, and more particularly to devices that support nostril air passageways.

2. Description of the Prior Art

The benefits of increasing air volume effectiveness during nasal breathing are widely known, Snoring is reduced, breathing is less labored, and the tendency to breathe through the mouth is reduced.

There are other nasal devices used for maintaining airflow through the nostrils.

U.S. Pat. No. 1,256,188, issued to G. H. Wilson, includes a device having connected tubes for insertion into the nostrils. The tubes have a smooth exterior surface and do not have inwardly tapered forward ends and rearward ends.

U.S. Pat. No. 4,221,217, issued to Saul O. Amezcus, includes rigidly joined members for insertion in the nostrils that have smooth exterior surfaces and do not have inwardly tapered forward ends and rearward ends. The members are funnel-shaped along the length of the members until the forward end is reached, at which point a right-angled forward end is presented.

U.S. Pat. No. 2,569,743, issued to M. P. Carlock, includes independent tubes for insertion into the nostrils that have an enlarged forward end portion resulting in a prominently sized shoulder positioned on the tube. Substantially enlarged structure is positioned at the rearward end for engaging structure that joins two of the tubes. The enlarged forward end portion has a forward end taper. The exterior surface is smooth.

U.S. Pat. No. 2,672,138, issued to M. P. Carlock, includes tubes for insertion into the nostrils that have a smooth exterior surface, a bulging protrusion along the exterior surface for fitting in the pocket or nest of the interior of the lobe of the nostril. The protrusion does not extend along the entire perimeter of the tubes and is only partially present at the tube forward end. All, or substantially all, of the tube forward ends do not have an inward taper.

U.S. Pat. No. 3,424,152, issued to I. D. Kuhlman, includes tubes for insertion into the nostrils and separate thin sheets of absorbent cotton for wrapping the tubes.

U.S. Pat. No. 3,935,859, issued to Donald E. Doyle is a surgical nasal splint that includes two tubes, mounted to two joined limbs, each limb having a flat plate part with a contour designed to fit the septum of the user. The plate part has a top edge that is convexly curved and lower edge that is nearly straight. The tubes do not have tapered forward or rearward ends.

No prior nasal devices have optimally addressed the problem of presenting a right-angled forward end and right-angled rearward end as the device is inserted and removed from the nostril. The abrupt ending causes unnecessary and uncomfortable disruption and dislocation of the sensitive tissue of the nostril interior wall. Furthermore, no prior nasal devices have avoided placing an extensive amount of smooth surface area against the nostril interior walls, creating an unnecessary tendency for drying and sticking of the nostril interior wall tissue to the device.

What is needed is a nasal device that has a resilient tube for insertion into the nostril, which has an inwardly tapered forward end and an inwardly tapered rearward end, and an exterior surface area with nonconformities distributed across most of such area, so that the contact of the tube exterior surface is discontinuous between such nonconformities.

SUMMARY OF THE PRESENT INVENTION

The present invention is a nasal device for insertion into nostrils. The device overcomes the shortcomings of the prior art by providing tubes for insertion that have inwardly tapered forward and rearward tube ends, such that neither end presents a right-angled, abrupt profile against the nostril interior wall tissue. The tubes have nonconformities distributed substantially uniformly across the exterior surfaces of each tube, The nonconformities cause discontinuities in the contact between the tube exterior surface and the nostril interior wall tissues, thus reducing the drying and sticking that can otherwise occur when significant amount of smooth surface areas are placed against such tissues over an extended period of time.

The present invention includes forward and rearward end tapers that are flat, arcuate, and arcuate to the extent that a semicircular cross-section profile is presented.

The tube exterior surface nonconformities can be mound-shaped, including bubble-shaped, ridge-shaped, or other shapes, and can be of uniform or varying size. The nonconformities can be substantially aligned on the exterior surface, or positioned at random. These nonconformities on the exterior surface area are resilient and substantially permanent in shape and position, although an embodiment with inelastic nonconformities is also provided.

An air passage device is provided for insertion into nostrils, the nostrils having interior wall surfaces, comprising: a pair of generally circular tube members, each tube member having an air passageway and an exterior surface, each tube member being sized to be received by a nostril, the exterior surface having nonconformities, such that each tube member's exterior surface's contact with the nostril interior wall surface is discontinuous, the nonconformities being distributed across the exterior surface in a substantially uniform manner across the exterior surface; and a connection member for connecting the tube members.

In one embodiment of the above-described device, the nonconformities are generally mound-shaped, In another embodiment of the above-described device the mound-shaped nonconformities are randomly positioned on the exterior surface.

In one embodiment of the above-described device the mound-shaped nonconformities are substantially aligned on the exterior surface.

In another embodiment of the above-described device the mound-shaped nonconformities are bubble-shaped.

In another embodiment of the above described device, the nonconformities are substantially uniform in size.

In another embodiment of the above-described device, the nonconformities are variously sized.

In another embodiment of the above-described device, the nonconformities are concentrically positioned ridges.

In another embodiment of the above-described device, the nonconformities are resilient.

In another embodiment of the above described device, the nonconformities are inelastic.

In another embodiment of the above-described device, the tubes are resilient.

In another embodiment of the above-described device, the tubes are inelastic.

In another embodiment of the above-described device, each tube member further has a forward end, the forward end being tapered.

In another embodiment of the above-described device, each tube member further has a rearward end, the rearward end being tapered.

In another embodiment of the above-described device, each tube member further has a forward end and a rearward end, the forward end and the rearward end being tapered.

In another embodiment of the above-described device, the connection member is flexible.

In another embodiment of the above-described device, the connection member is inflexible.

An air passage device is provided for insertion into nostrils, comprising: a pair of generally circular tube members, each tube member having an air passageway, a forward end, and a rearward end, each tube member being sized to be received by a nostril, the forward end of each tube member being tapered inwardly in the forward direction, the rearward end of each tube member being tapered inwardly in the rearward direction; and a connection member for connecting the tube members.

In another embodiment of the foregoing device, the forward and rearward end tapers are substantially flat.

In another embodiment of the above-described device, the forward and rearward end tapers are arcuate.

In another embodiment of the above-described device, the forward and rearward end tapers are arcuate and extend such that the forward end and rearward end are both semicircular in cross-sectional profile.

In another embodiment of the above-described device, the connection member is flexible.

In another embodiment of the above-described device, the connection member is inflexible.

An air passage device is provided for insertion into nostrils, the nostrils having interior wall surfaces, comprising: a pair of generally circular tube members, each tube member being sized to be received by a nostril, each tube member having an air passageway, means for minimizing nostril interior wall resistance during insertion into the nostril, and means for minimizing nostril interior wall resistance during removal from the nostril; and a connection member for connecting the tube members.

In another embodiment of the foregoing device, the means for minimizing nostril interior wall resistance during insertion comprises the tube member, the tube member having a forward end, the forward end being tapered, and further wherein the means for minimizing nostril interior wall resistance during removal comprises the tube member, the tube member further having a rearward end, the rearward end being tapered.

An air passage device is provided for insertion into nostrils, the nostrils having interior wall surfaces, comprising: a pair of generally circular tube members, each tube member being sized to be received by a nostril, each tube member having an air passageway and means for reducing tube member contact with the nostril interior walls; and means for connecting the tube members.

In another embodiment of the foregoing device, the means for reducing tube member contact with the nostril interior walls comprises the tube member, the tube member having an exterior surface, the exterior surface having nonconformities such that each tube member's exterior surface's contact with the nostril wall is discontinuous, the nonconformities being distributed across the exterior surface in a substantially uniform manner.

An air passage device is provided for insertion into a nostril, the nostrils having interior wall surfaces, comprising, a generally circular tube member, the tube member having an air passageway and an exterior surface, the tube member being sized to be received by a nostril, the exterior surface having nonconformities, such that the tube member's exterior surface's contact with the nostril interior wall surface is discontinuous, the nonconformities being distributed across the exterior surface in a substantially uniform manner across the exterior surface, and a retrieval member, the retrieval member being attached to the tube and sized to protrude from the nostril following insertion of the tube.

In another embodiment of the foregoing device, the tube member further has a forward end and a rearward end, the forward end and the rearward end being tapered.

The foregoing and other advantages will appear from the description to follow. In the description reference is made to the accompanying drawings, which form a part hereof, and in which is shown by way of illustration, specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE REFERENCED NUMERALS

Figure 1:
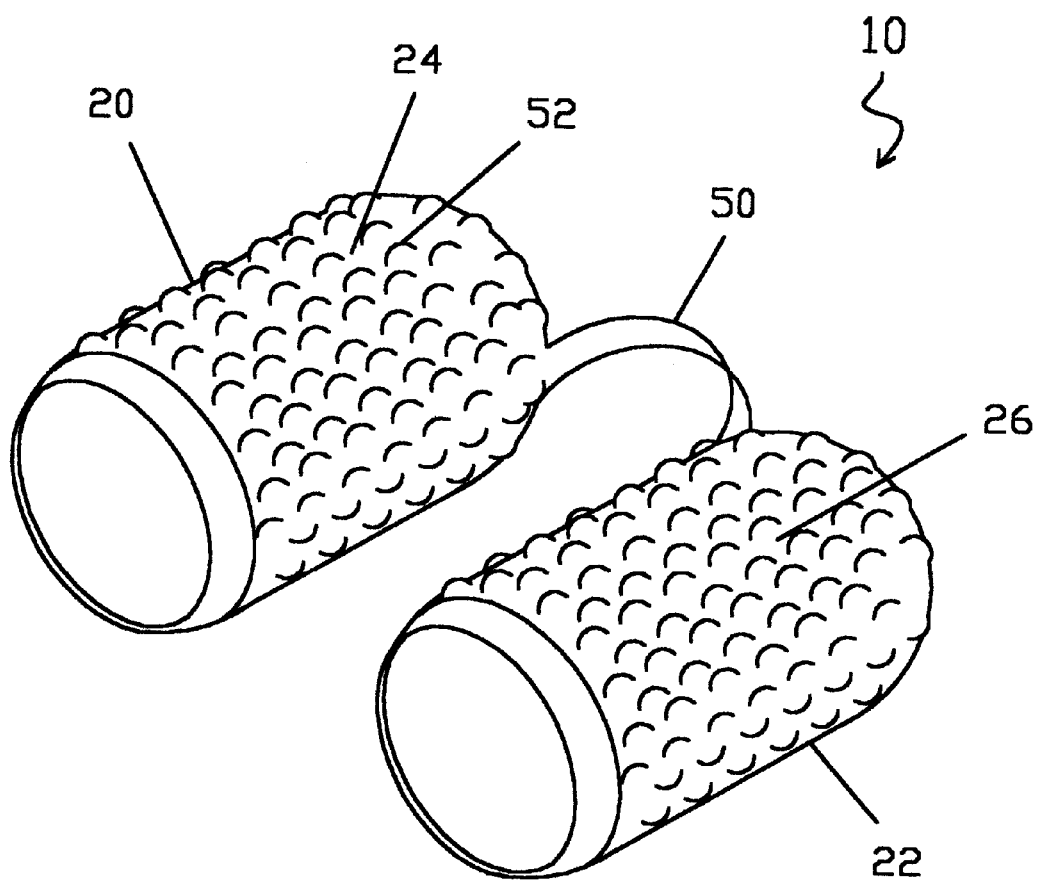
FIG. 1 is an oblique view of the preferred embodiment of the present invention.

Turning now descriptively to the drawings, in which similar reference characters denote similar elements throughout the several views, the figures illustrate the nasal air passage device of the present invention. With regard to the reference numerals used, the following numbering is used throughout the various drawing figures.

10 nasal air passage device of the present invention
20 left tube
22 right tube
24 left tube exterior surface
26 right tube exterior surface
28 nostrils
30 nostril interior wall
32 left tube forward end
34 right tube forward end
36 left tube rearward end
38 right tube rearward end
40 flat taper
42 arcuate taper
44 semi-circular taper
50 connection member
52 mound-shaped nonconformities
54 bubble-shaped nonconformities
56 ridge-shaped nonconformities
60 single tube
62 single tube forward end
64 single tube rearward end
66 single tube surface area
68 single tube retrieval member

DETAILED DESCRIPTION

Turning now descriptively to the drawings, in which similar reference characters denote similar elements throughout the several views, FIGS. 1–14 illustrate the Nasal Air Passage Device of the present invention indicated generally by the numeral 10.

Figure 11:
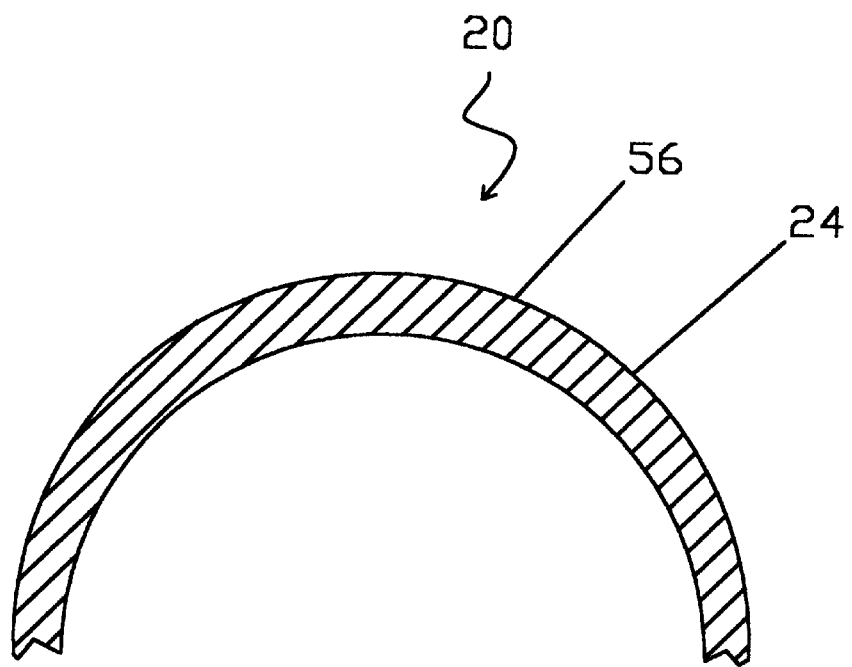
FIG. 11 is a sectional side view of the embodiment of FIG. 10, cut along cutting plane 11—11 as shown on FIG. 10.
Figure 12:
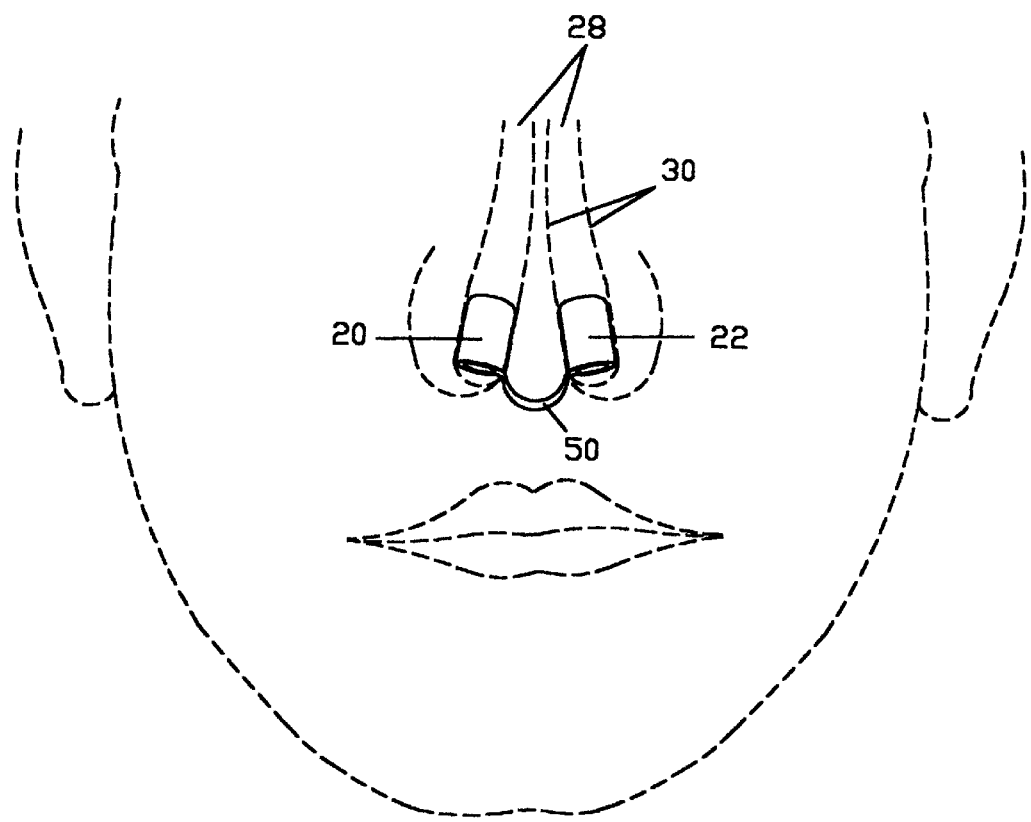
FIG. 12 is an oblique view depicting the device in use, with the front portion of the nose removed for viewing the device.
Figure 13:
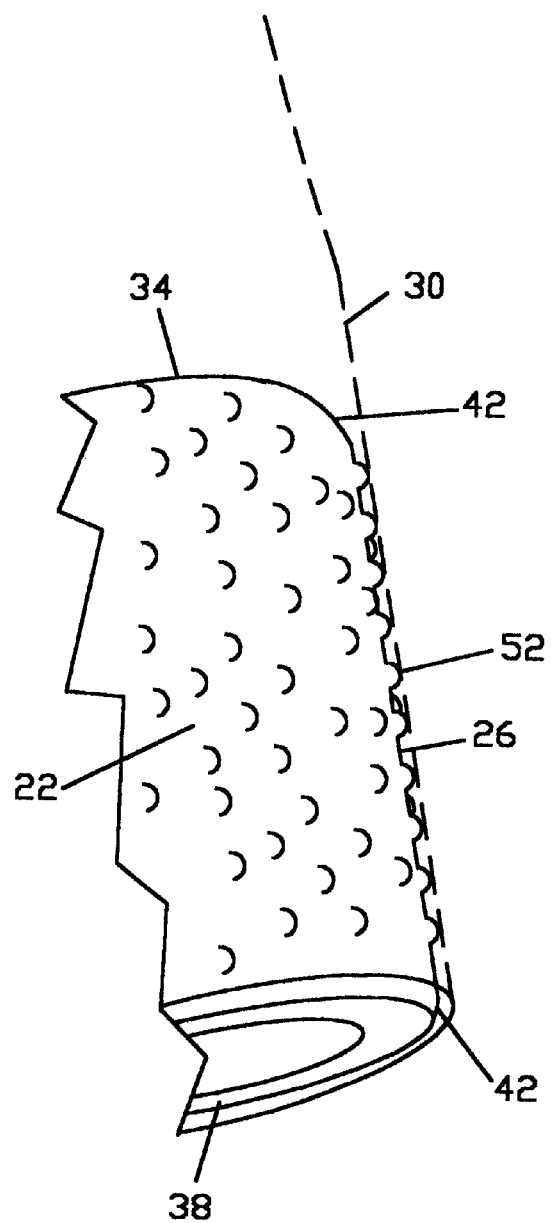
FIG. 13 is partial cutaway view showing the device against a nostril interior wall.
Figure 14:
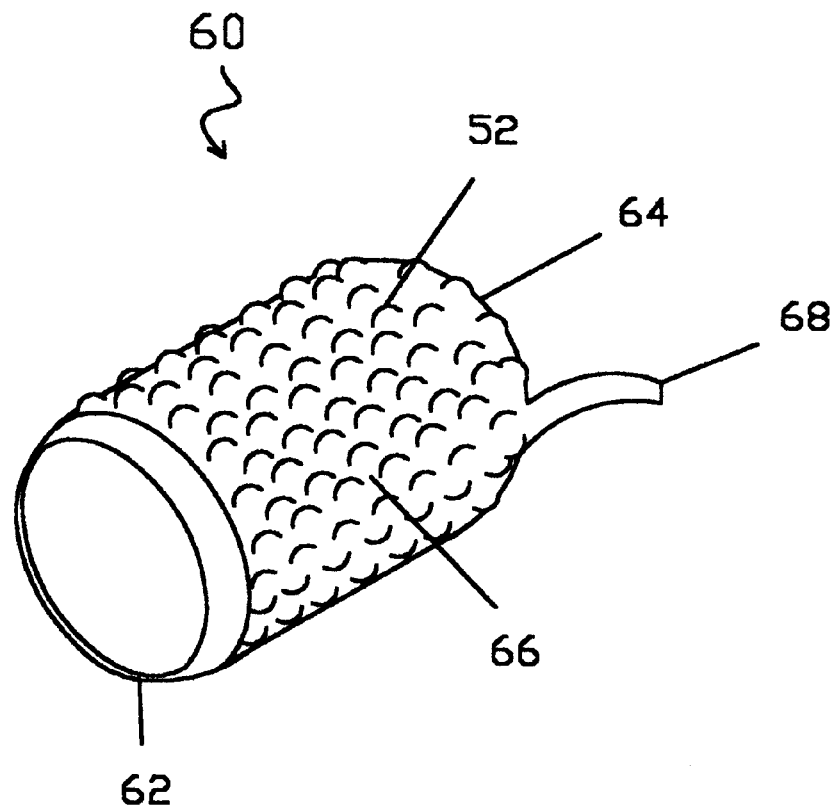
FIG. 14 is an oblique view of an alternate embodiment providing only one tube with a retrieval member.

Various embodiments of the Nasal Air Passage Device 10 are shown in FIGS. 1–14. FIGS. 12–13 depict the device 10 in use.

A pair of generally circular tubes 20,22 is provided. The left tube 20 and the right tube 22, each have an exterior surface 24,26. The tubes 20,22 are sized to be insertable within a typical nostril 28. The tubes 20,22 are constructed, at least in part, of a plastic having sufficient rigidity to slightly displace and retain the nostril interior walls 30. The tubes 20,22 can be resilient or inelastic.

Figure 4:
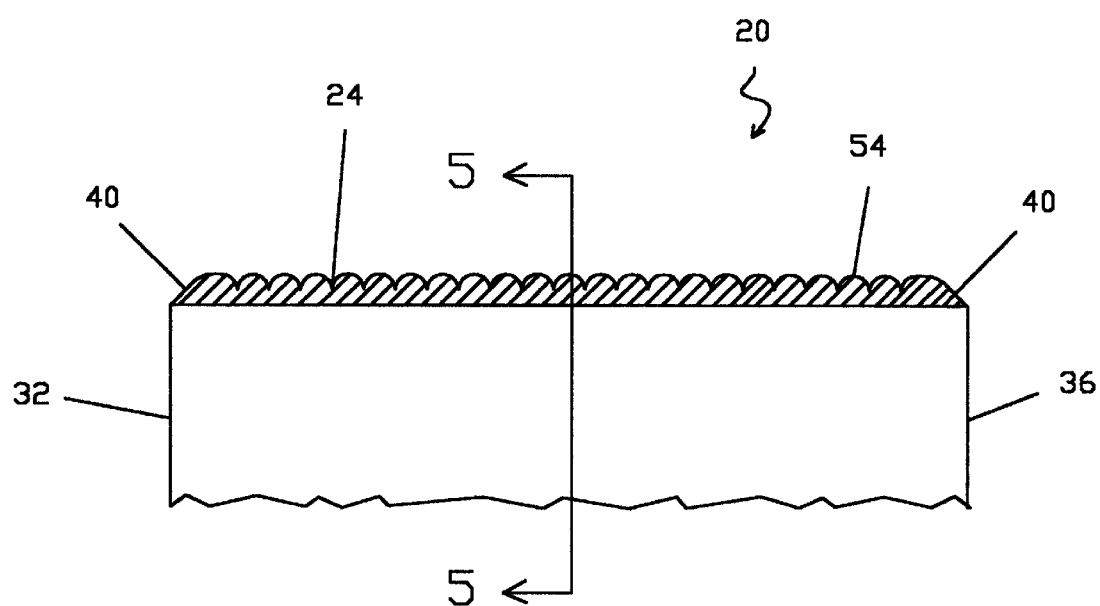
FIG. 4 is a sectional side view of an embodiment of the device.
Figure 5:
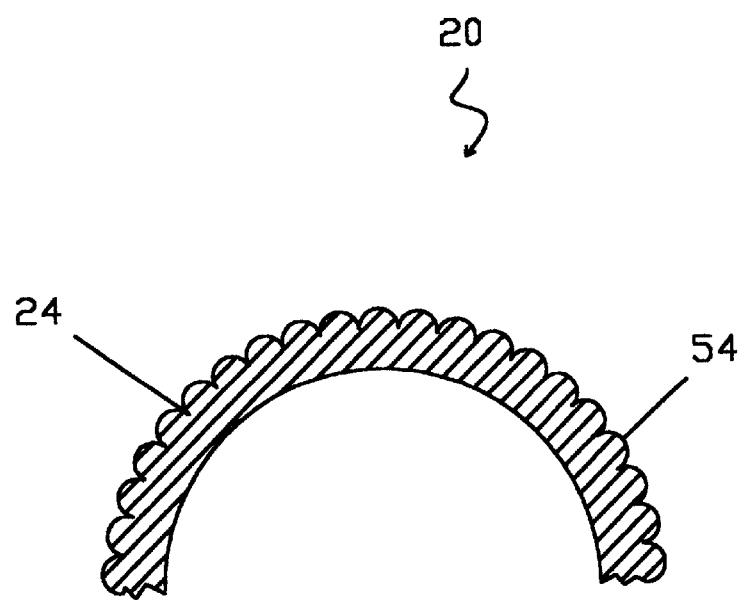
FIG. 5 is a sectional side view of the embodiment of FIG. 4, cut along cutting plane 5—5 as shown on FIG. 4.
Figure 6:
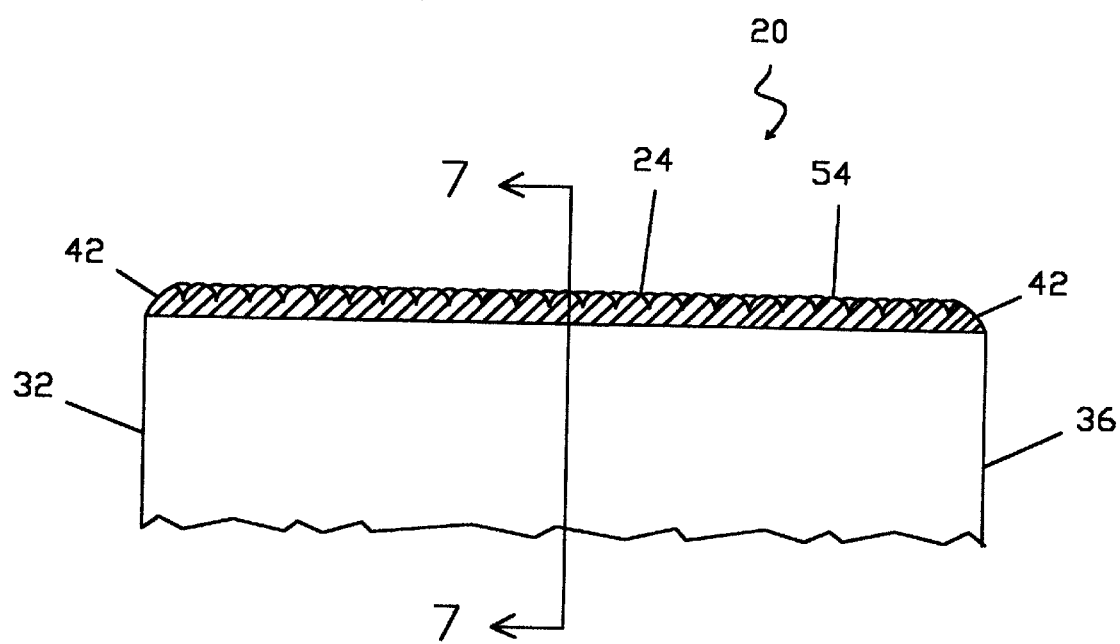
FIG. 6 is a sectional side view of an embodiment of the device.
Figure 7:
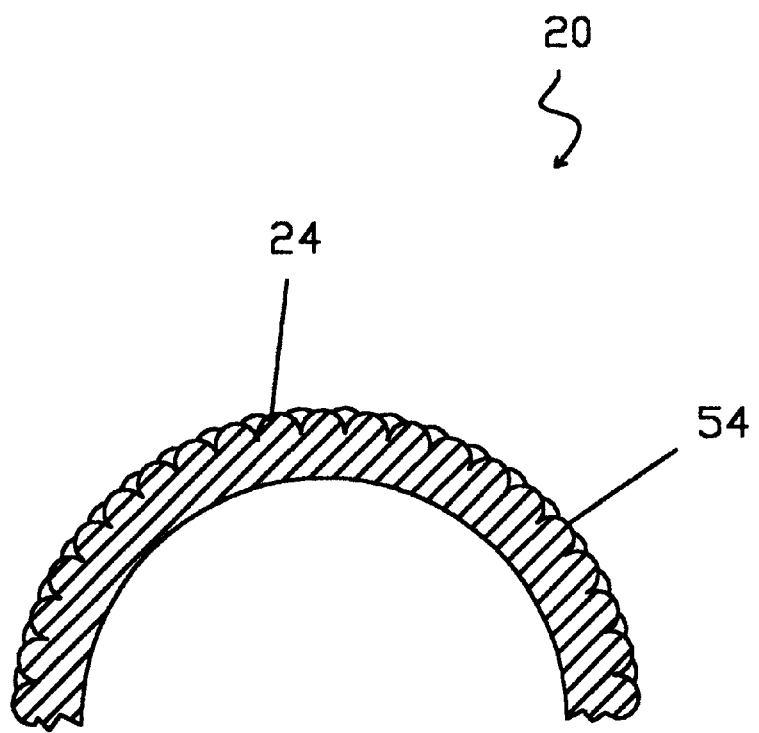
FIG. 7 is a sectional side view of the embodiment of FIG. 6, cut along cutting plane 7—7 as shown on FIG. 6.
Figure 8:
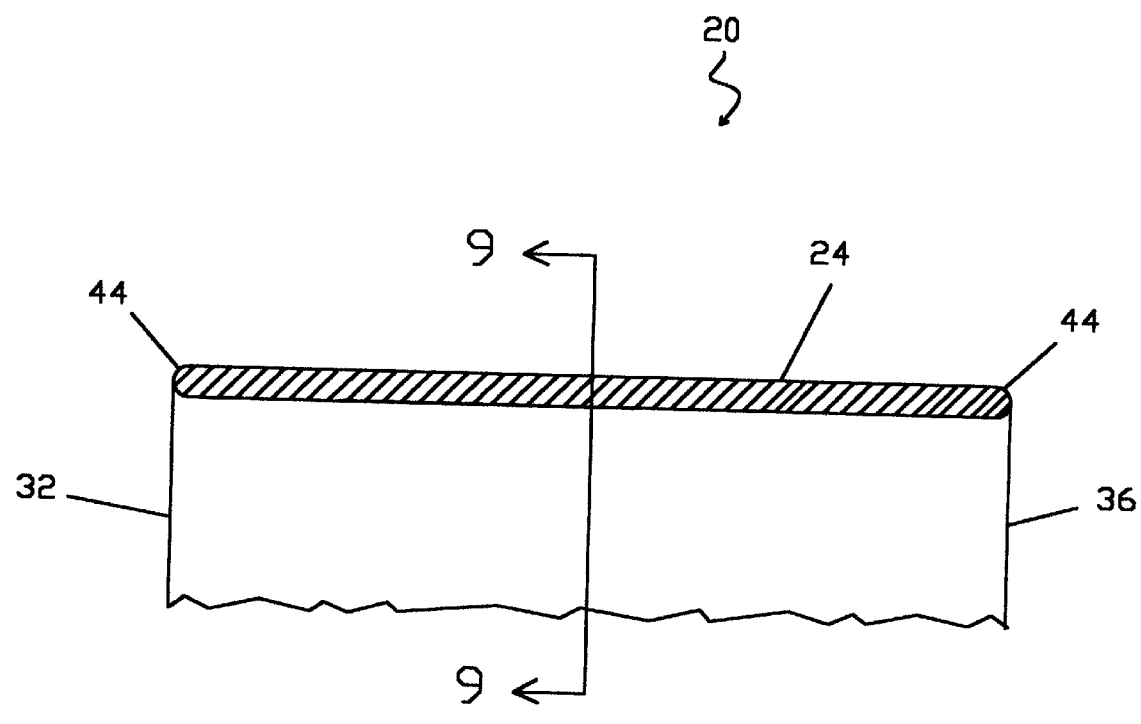
FIG. 8 is a sectional side view of an embodiment of the device.
Figure 9:
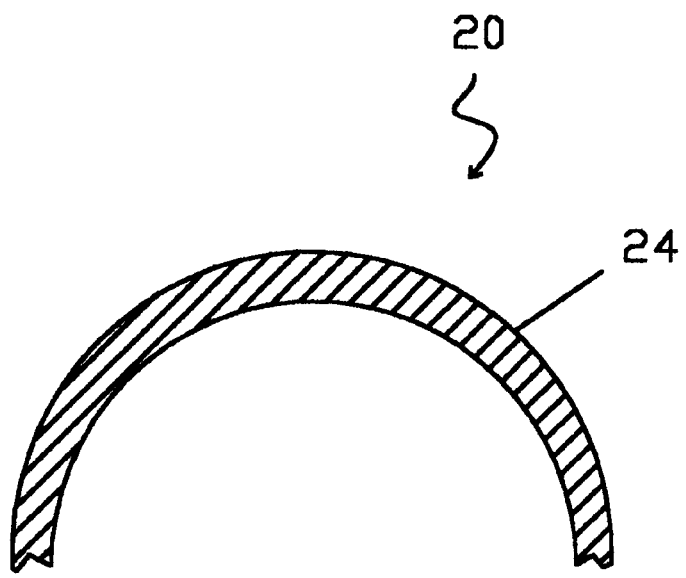
FIG. 9 is a sectional side view of the embodiment of FIG. 8, cut along cutting plane 9—9 as shown on FIG. 8.
Figure 10:
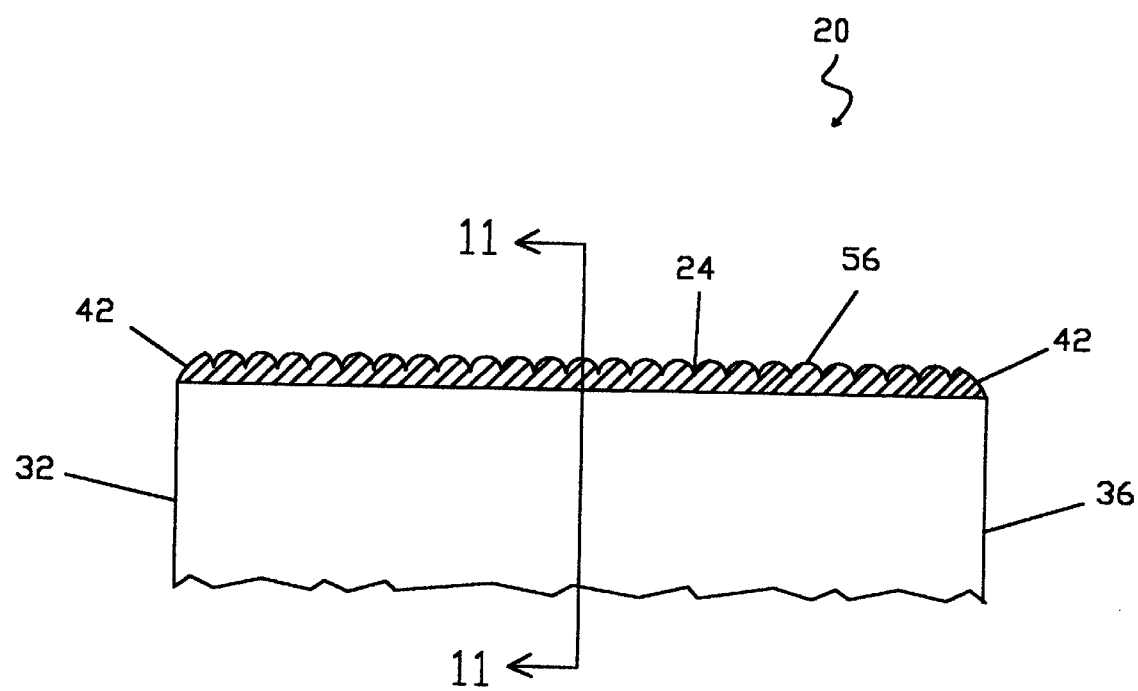
FIG. 10 is a sectional side view of an embodiment of the device.

Each tube has a forward end 32,34 and a rearward end 36,38. Each forward end 32,34 tapers inwardly, as shown from the top in FIG. 2 and in sectional side views in FIGS. 4,6,8, and 10. The taper 40 shown in FIG. 4 is substantially flat. FIG. 6 depicts a taper.42 that is arcuate, and FIG. 8 depicts a taper 44 that is arcuate, with the arc continuing to form the generally semicircular cross-sectional profile shown.

In use, and particularly during insertion, the forward end 32,34 prevents an otherwise right-angled forward end 32,34 from disruptively interacting with the delicate tissue of the nostril interior walls 30. Instead, such tissue is only minimally dislocated, with that dislocation being more uniformly distributed across the tube exterior surface area 24,26.

Similarly, the rearward end 36,38, reduces the dislocation of the nostril interior wall 30 tissue during removal.

Furthermore, the tapered forward ends 32,34 and rearward ends 36,38 prevent a right-angled, shoulder from bearing uncomfortably upon the nostril interior walls, while in use following insertion, and prior to withdrawal. As used herein the term "mound" refers to elevations from the tube surface having a generally non-elongated top profile, and exclude ridges and other elevations that extend in an elongated fashion over the tube surface. The term "concentrically," refers to nonconformities that extend about the circumference of the tube to form a generally circular profile with common centers proximate the longitudinal axis of the tube.

Figure 2:
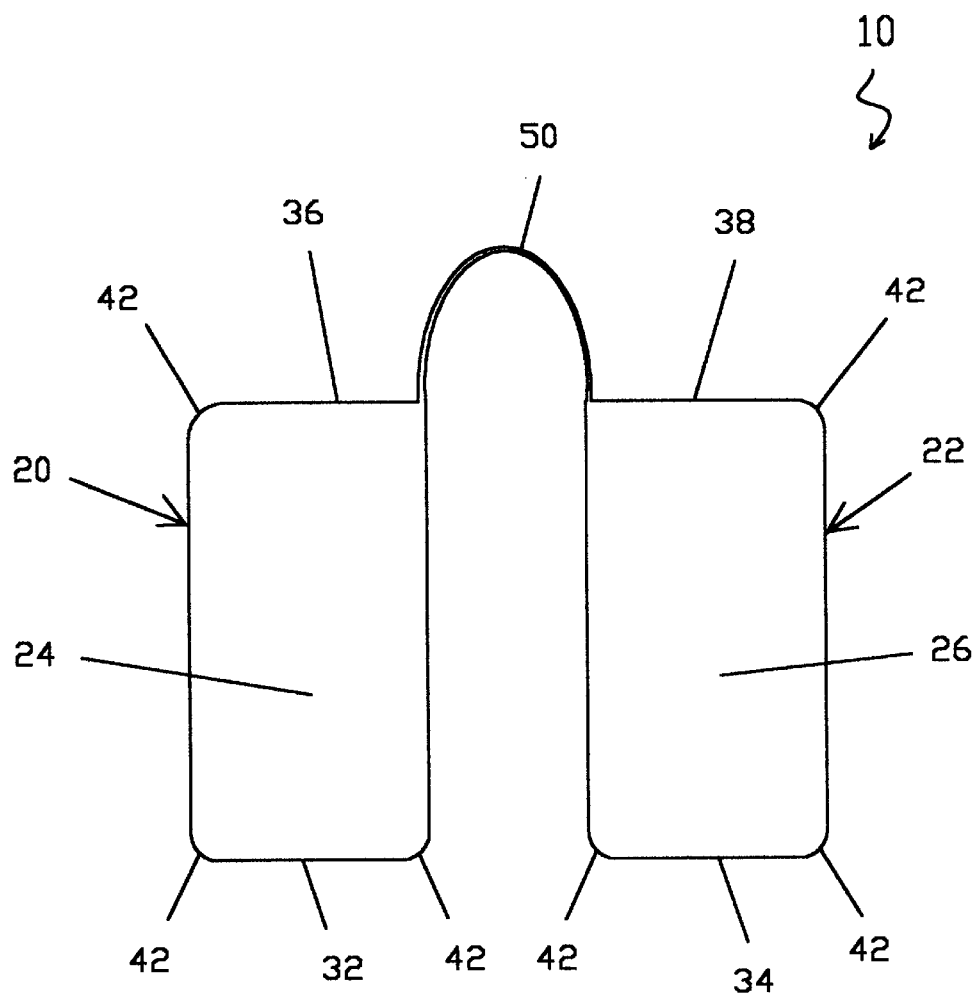
FIG. 2 is a top view of the device.
Figure 3:
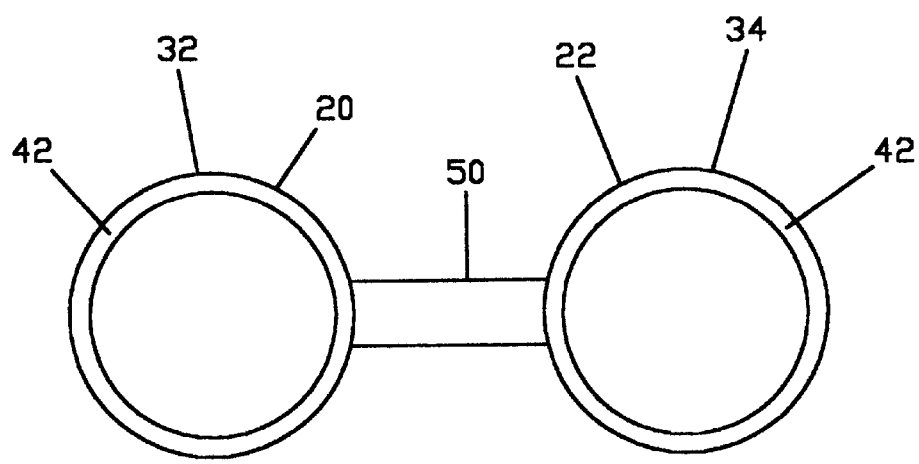
FIG. 3 is a front view of the device, depicting the forward ends.

As shown in FIGS. 1–2 and 12, a connection member 50 connects the tubes 20,22. The connection member 50 is constructed from either a flexible or stiff plastic. A stiffer connection member 50 encourages retention of the tubes 20,22 within the nostrils 28, in that the tubes 20,22 are urged by a properly sized connection member 50 against one side of each nostril's interior walls 30. The connection member 50 is of sufficient length to allow both tubes 20,22 to be inserted fully in the nostrils 28.

In the preferred embodiment of the present invention, each tube's exterior surface 24,26 has nonconformities 52,54,56 that are distributed across the exterior surface 24,26 in a substantially uniform manner. As shown in FIG. 13, these nonconformities 52,54,56 interrupt the otherwise substantially continuous contact between the exterior surface 24,26 and the nostril interior walls 30, thus reducing the tendency for the tube exterior surface 24,26 to stick to the nostril interior walls 30, and reducing the likelihood of the tube 20,22 slipping from the nostrils 28.

In the preferred embodiment, generally mound-shaped nonconformities 52 are provided, including bubble-shaped nonconformities 54. These can be either randomly positioned on the exterior surface 24,26, as shown in FIG. 1, or be positioned in aligned rows and offset rows, as shown in FIGS. 4 and 6. The size of such nonconformities 52,54,56 can be uniform or varied. In other embodiments, concentrically positioned, ridge-shaped nonconformities 56 are provided, as shown in FIG. 11. The nonconformities 52,54, 56 can be resilient or inelastic. In other embodiments, the exterior surfaces 24,26 are substantially smooth, as shown in FIGS. 2–3 and 8–9.

In another embodiment only a single tube 60 is used. The forward end 62 and rearward end 64 are variously tapered, and the surface area 66 has various nonconformities, as disclosed above. A retrieval member 68 is attached in a manner similar to connection member 50, allowing the user to neatly remove the tube 60, by grasping the retrieval member 68 with two fingers.

Although particular types of materials and particular dimensions have been discussed herein, other types and sizes of materials, such as various types of plastic, rubber, and the like, can also be used, all in accordance with the present invention, and as determined by the intended end use for the overall device, as will occur to those of skill in the art upon review of the present disclosure.

While certain novel features of this invention have been shown and described and are pointed out in the annexed claims, it is not intended to be limited to the details above, since it will be understood that various omissions, modifications, substitutions and changes in the forms and details of the device illustrated and in its use can be made by those skilled in the art without departing in any way from the spirit of the present invention.

Without further analysis, the foregoing will so fully reveal the gist of the present invention that others can, by applying current knowledge, readily adapt it for various nasal air passage applications without omitting features that, from the standpoint of prior art, fairly constitute essential characteristics of the generic or specific aspects of this invention.

What is claimed as new and desired to be protected by Letters Patent is set forth in the appended claims:

1. An air passage device for insertion into nostrils, the nostrils having interior wall surfaces, comprising:

a pair of generally cylindrical tube members, each tube member having an air passageway, a forward end, a rearward end, a cylindrical axis, a longitudinal length, and an exterior surface, each tube member being sized to be received by a nostril, the exterior surface having nonconformities, such that each tube member's exterior surface's contact with the nostril interior wall surface is discontinuous, the nonconformities being distributed across the exterior surface in a substantially uniform manner across the exterior surface, the nonconformities being discontinuous along the tube longitudinal length, the forward end of each tube member being tapered inwardly and concentrically about such tube member's cylindrical axis in the forward direction, the rearward end of each tube member being tapered inwardly and concentrically about such tube member's cylindrical axis in the rearward direction; and a connection member for connecting the tube members.

2. The device of claim 1, wherein the nonconformities are generally mound-shaped.

3. The device of claim 2, wherein the mound-shaped nonconformities are randomly positioned on the exterior surface.

4. The device of claim 2, wherein the mound-shaped nonconformities are substantially aligned on the exterior surface.

5. The device of claim 2, wherein the mound-shaped nonconformities are bubble-shaped.

6. The device of claim 1, wherein the nonconformities are substantially uniform in size.

7. The device of claim 1, wherein the nonconformities are variously sized.

8. The device of claim 1, wherein the nonconformities are concentrically positioned ridges.

9. The device of claim 1, wherein the nonconformities are resilient.

10. The device of claim 1, wherein the nonconformities are inelastic.

11. The device of claim 1, wherein the tubes are resilient.

12. The device of claim 1, wherein the tubes are inelastic.

13. The device of claim 1, wherein the connection member is flexible.

14. The device of claim 1, wherein the connection member is inflexible.

15. An air passage device for insertion into nostrils, comprising:

a pair of generally cylindrical tube members, each tube member having an air passageway, a forward end, and a rearward end, each tube member having a cylindrical axis, each tube member being sized to be received by a nostril, the forward end of each tube member being tapered inwardly and concentrically about such tube member's cylindrical axis in the forward direction, the rearward end of each tube member being tapered inwardly and concentrically about such tube member's cylindrical axis in the rearward direction; and a connection member for connecting the tube members.

16. The device of claim 15, wherein the forward and rearward end tapers are substantially flat.

17. The device of claim 15, wherein the forward and rearward end tapers are arcuate.

18. The device of claim 15, wherein the forward and rearward end tapers are arcuate and extend such that the forward end and rearward end are both semicircular in cross-sectional profile.

19. The device of claim 15, wherein the connection member is flexible.

20. The device of claim 15, wherein the connection member is inflexible.

21. An air passage device for insertion into nostrils, the nostrils having interior wall surfaces, comprising:

a pair of generally circular tube members, each tube member being sized to be received by a nostril, each tube member having an air passageway, means for minimizing nostril interior wall resistance during insertion into the nostril, and means for minimizing nostril interior wall resistance during removal from the nostril; and a connection member for connecting the tube members.

22. An air passage device for insertion into nostrils, the nostrils having interior wall surfaces, comprising:

a pair of generally cylindrical tube members, each tube member being sized to be received by a nostril, each tube member having an air passageway, a forward end, a rearward end, a cylindrical axis, and means for reducing tube member contact with the nostril interior walls, the forward end of each tube member being tapered inwardly and concentrically about such tube member's cylindrical axis in the forward direction, the rearward end of each tube member being tapered inwardly and concentrically about such tube member's cylindrical axis in the rearward direction; and means for connecting the tube members.

23. The device of claim 22, wherein the means for reducing tube member contact with the nostril interior walls comprises the tube member, the tube member having an exterior surface, the exterior surface having nonconformities such that each tube member's exterior surface's contact with the nostril wall is discontinuous, the nonconformities being distributed across the exterior surface in a substantially uniform manner.

24. An air passage device for insertion into nostrils, the nostrils having interior wall surfaces, comprising, a generally cylindrical tube member, the tube member having an air passageway, a forward end and a rearward end, the tube member having a cylindrical axis, the tube member being sized to be received by a nostril, the forward end of each tube member being tapered inwardly and concentrically about such tube member's cylindrical axis in the forward direction, the rearward end of each tube member being tapered inwardly and concentrically about such tube member's cylindrical axis in the rearward direction, and a retrieval member, the retrieval member being attached to the tube and sized to protrude from the nostril following insertion of the tube.

* * * * *